US010640827B2

(12) United States Patent
Lee et al.

(10) Patent No.: US 10,640,827 B2
(45) Date of Patent: May 5, 2020

(54) FABRICATION OF WEDGE SHAPED ELECTRODE FOR ENHANCED DNA SEQUENCING USING TUNNELING CURRENT

(71) Applicant: SEAGATE TECHNOLOGY LLC, Cupertino, CA (US)

(72) Inventors: Kim Yang Lee, Fremont, CA (US); David S. Kuo, Palo Alto, CA (US); Thomas Young Chang, Menlo Park, CA (US); Xiaomin Yang, Livermore, CA (US); ShuaiGang Xiao, Fremont, CA (US); Koichi Wago, Sunnyvale, CA (US)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 74 days.

(21) Appl. No.: 15/886,661

(22) Filed: Feb. 1, 2018

(65) Prior Publication Data

US 2018/0216180 A1  Aug. 2, 2018

Related U.S. Application Data

(60) Provisional application No. 62/453,365, filed on Feb. 1, 2017.

(51) Int. Cl.
*C12Q 1/6874* (2018.01)
*G01N 33/487* (2006.01)
(Continued)

(52) U.S. Cl.
CPC ..... *C12Q 1/6874* (2013.01); *G01N 27/44791* (2013.01); *G01N 33/48721* (2013.01); *C12Q 1/6869* (2013.01)

(58) Field of Classification Search
CPC .. C12Q 1/6874; G01N 27/44791; H01J 37/00
See application file for complete search history.

(56) References Cited

U.S. PATENT DOCUMENTS 5,007,984 A * 4/1991 Tsutsumi ................. C23F 1/02
216/103
5,071,714 A * 12/1991 Rodbell ............. H01L 21/4846
204/192.17
(Continued)

FOREIGN PATENT DOCUMENTS

WO  WO 2015057870  *  4/2015

OTHER PUBLICATIONS

Di Ventra, Massimiliano, et al., "Decoding DNA, RNA and peptides with quantum tunneling," Nature Nanotechnology, vol. 11, Feb. 2016, pp. 117-126.
(Continued)

*Primary Examiner* — Narayan K Bhat
(74) *Attorney, Agent, or Firm* — Holzer Patel Drennan

(57) ABSTRACT

A DNA sequencing device, and related methods, include a nanochannel sized to receive a DNA strand, a first electrode member exposed within the nanochannel, and a second electrode member exposed within the nanochannel and spaced apart from the first electrode to form an electrode gap. The second electrode member has a wedge shaped profile, and the first and second electrode members are operable to detect a change in electronic signal as the DNA strand passes through the electrode gap.

13 Claims, 7 Drawing Sheets

(51) Int. Cl.
    *G01N 27/447*      (2006.01)
    *C12Q 1/6869*      (2018.01)

(56) References Cited

U.S. PATENT DOCUMENTS

| | | | |
|---|---|---|---|
| 5,127,989 A * | 7/1992 | Haraguchi | G03F 7/2022 |
| | | | 216/49 |
| 6,627,067 B1 | 9/2003 | Branton et al. | |
| 7,582,490 B2 | 9/2009 | Golovchenko et al. | |
| 8,105,471 B1 | 1/2012 | Han et al. | |
| 9,410,923 B2 | 8/2016 | Sauer et al. | |
| 10,247,700 B2 * | 4/2019 | Hu | G01N 27/44791 |
| 10,413,903 B2 | 9/2019 | Taniguchi | |
| 2002/0039737 A1 | 4/2002 | Chan et al. | |
| 2010/0188109 A1 | 7/2010 | Edel | |
| 2010/0267158 A1 * | 10/2010 | Chou | B01L 3/502761 |
| | | | 436/94 |
| 2011/0174629 A1 | 7/2011 | Bouchet et al. | |
| 2013/0334047 A1 | 12/2013 | Jeong et al. | |
| 2014/0151228 A1 | 6/2014 | Royyuru et al. | |
| 2014/0312002 A1 | 10/2014 | Peng | |
| 2016/0153105 A1 | 6/2016 | Gumbercht | |
| 2016/0319342 A1 | 11/2016 | Kawai | |
| 2017/0144158 A1 | 5/2017 | Taniguchi | |
| 2017/0146510 A1 | 5/2017 | Ikeda et al. | |
| 2017/0253479 A1 | 9/2017 | Nikoobakht, IV | |
| 2018/0120287 A1 | 5/2018 | Henck | |

OTHER PUBLICATIONS

Feng, Yanxiao, et al., "Nanopore-based Fourth-generation DNA Sequencing Technology," Genomics Proteomics Bioinformatics, 13 (2015), pp. 4-16.

Ivanov, A.P., et al., "DNA Tunneling Detector Embedded in a Nanopore," Nano Letters, 2011, 11, pp. 279-285.

KE, Rongqin, et al., "Fourth Generation of Next-Generation Sequencing Technologies: Promise and Consequences," Human Mutation, vol. 37, No. 12, 2016, pp. 1363-1367.

Kulski, Jerzy K., "Next-Generation Sequencing—An Overview of the History, Tools, and 'Omic' Applications," http://dx.doi.org/10.5772/61964, 59 pages.

Duan et al., "Review article: Fabrication of nanofluidic devices," Biomicrofluidics 7, 026501 (2013).

\* cited by examiner

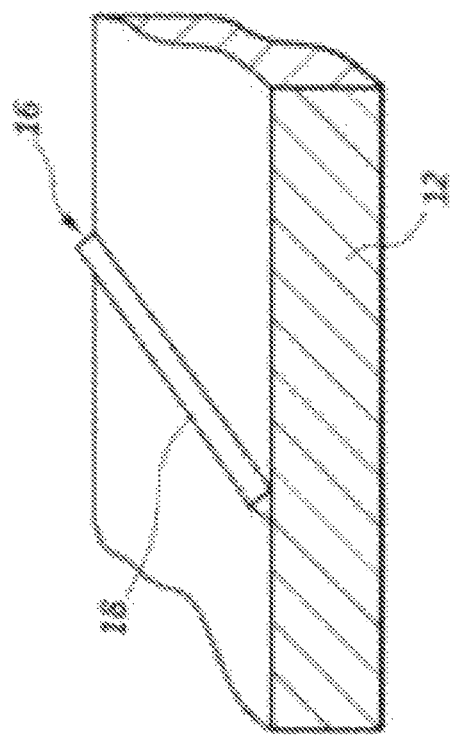
FIG. 2E
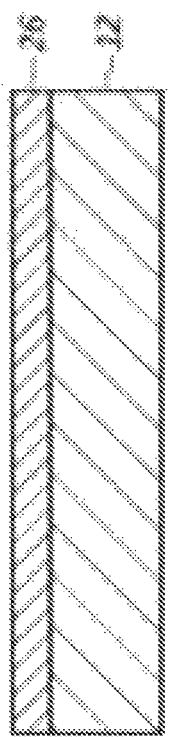
FIG. 2A
FIG. 2B
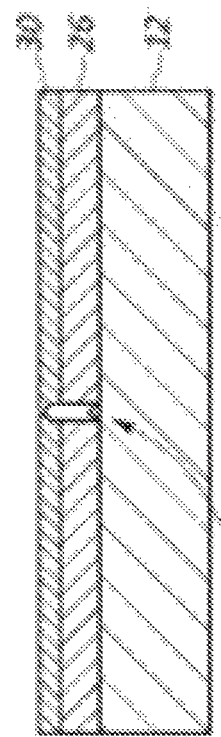
FIG. 2C
FIG. 2D

FABRICATION OF WEDGE SHAPED ELECTRODE FOR ENHANCED DNA SEQUENCING USING TUNNELING CURRENT

RELATED APPLICATIONS

This application claims the benefit of the filing date of U.S. Provisional Application No. 62/453,365, filed on 1 Feb. 2017, and entitled FABRICATION OF WEDGE SHAPED BOTTOM ELECTRODE FOR ENHANCED DNA SEQUENCING USING TUNNELING CURRENT, the disclosure of which is incorporated in its entirety by this reference.

SUMMARY

The present disclosure relates to nanoelectrodes and related fabrication methods for use in deoxyribonucleic acid (DNA) sequencing. The methods and devices disclosed herein include a tunneling electrode (e.g., an electrode having electrode members that are spaced apart by an initial gap size of about 10 nm or greater), wherein at least one of the electrode members has a wedge or pointed shape, which may help reduce noise in the measurement of an electronic signal collected by the nanoelectrode.

Another aspect of the present disclosure relates to a method of fabricating a nanoelectrode DNA sequencing device. The method includes forming a nanochannel structure, and forming a nanoelectrode for use with the nanochannel structure, the nanoelectrode having at least one electrode member with a wedge or pointed shape.

Another aspect of the present disclosure relates to a DNA sequencing device that includes a nanochannel sized to receive a DNA strand, a first electrode member exposed within the nanochannel, and a second electrode member exposed within the nanochannel and spaced apart from the first electrode to form an electrode gap. The second electrode member has a wedge shaped profile, and the first and second electrode members are operable to detect a change in electronic signal as the DNA strand passes through the electrode gap.

The electrode gap may be no greater than about 1 nm. The electrode gap may be in the range of about 0.3 nm to about 2 nm. The second electrode member may include a metal material. The first electrode member may include a planar surface exposed in the nanochannel. The second electrode member may have a tapered cross-sectional shape. The first and second electrode members may extend across an entire width of the nanochannel.

Another aspect of the present disclosure relates to a method of forming a DNA sequencing device. The method may include coating a substrate with a resist layer, patterning the resist layer to form a trench, depositing a conductive material on the resist layer and in the trench, the conductive material in the trench having a tapered profile, the conductive material forming a first electrode member, removing the conductive material from the resist layer and the resist layer from the substrate, and exposing a portion of the first electrode member in a nanochannel of the DNA sequencing device. The first electrode member may be configured to detect a change in electronic signal of a DNA strand passing through the nanochannel.

Patterning the resist layer may include using electron beam lithography for the patterning. Deposition of the conductive material may include directional deposition of the conductive material. Deposition of the conductive material may include thermal evaporation of the conductive material. Lifting off the conductive material may include dissolving the conductive material in a solvent. The method may further include trimming the first electrode member to sharpen the tapered profile of the first electrode member. Trimming the first electrode member may include using reactive ion etching (RIE) or ion beam etching (IBE) to remove portions of the first electrode member. The method may include forming a second electrode member, and exposing a portion of the second electrode member in the nanochannel at a location spaced apart from the first electrode member to form an electrode gap through which the DNA strand passes.

A further aspect of the present disclosure relates to a method of forming a DNA sequencing device. The method includes coating a substrate with a conductive layer, coating the conductive layer with a resist layer, patterning the resist layer to form a strip of resist material, pattern transferring the strip of resist material into the conductive layer, removing the resist material from the conductive layer to provide a first electrode member on the substrate, and trimming the first electrode member to have a tapered profile.

The pattern transferring may include using reactive ion etching (RIE) or ion beam etching (IBE) to remove portions of the conductive layer. Removing the resist material may include using $O_2$ reactive ion etching (RIE) to remove remaining portions of the resist material from the conductive layer. Trimming the first electrode member may include using ion beam etching (IBE) at multiple incident angles.

A still further aspect of the present disclosure relates to a method of DNA sequencing that includes providing a DNA sequencing device having a nanochannel and a nanoelectrode, the nanoelectrode having first and second electrode members exposed in the nanochannel and spaced apart with an electrode gap, the second electrode member having a wedge shaped profile, passing a DNA strand through the nanochannel and the electrode gap, detecting a change in electronic signal with the nanoelectrode as nucleotides of the DNA strand pass through the electrode gap, the wedge shaped profile of the second electrode member minimizing noise in the detected electronic signal, and determining an order of the nucleotides based on the detected electronic signals.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

FIGS. 2A-2E show steps of an additive process of forming an electrode member for a DNA sequencing device in accordance with the present disclosure.

DETAILED DESCRIPTION

Figure 1:
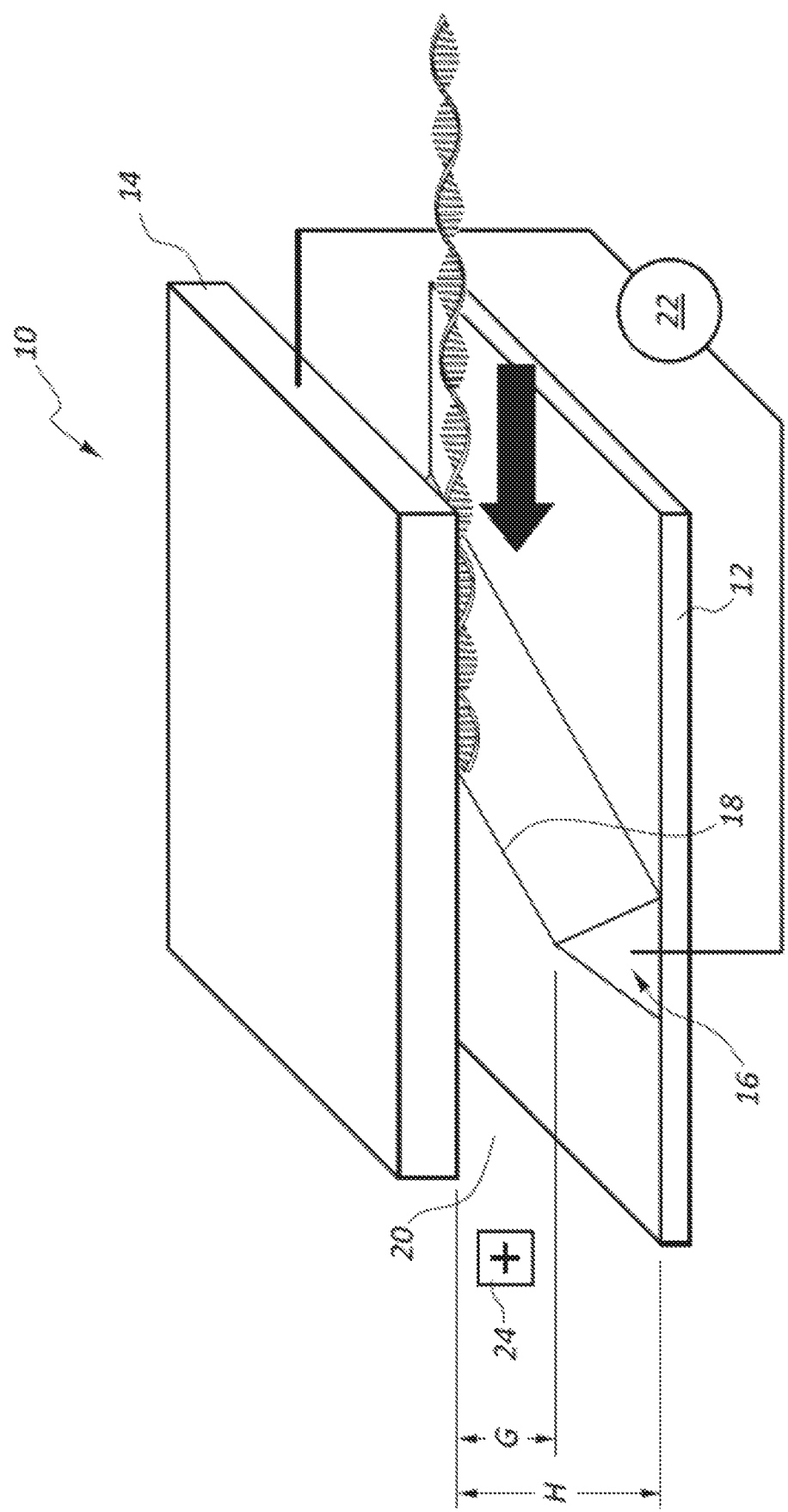
FIG. 1 shows an example DNA sequencing device in accordance with the present disclosure.

Despite considerable efforts, DNA sequencing today still suffers from high costs and low speeds. To address these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

Direct measure of individual nucleotides of long DNA strands rapidly and with low cost is one goal of DNA sequencing. Among these options, nanopore- and nanochannel-based approaches that measure a transverse signal across individual nucleotides have emerged as a promising approach. The general approach involves electrically driving DNA and RNA strands through a nanopore or narrow channel via ionic flow or driven by a pressure gradient. As the strand passes a high resolution sensor embedded inside the channel (e.g., a nanoelectrode), the high spatial resolution sensor measures the unique properties of the individual nucleotides (A,T,C,G). One type of sensor would consist of a conductive electrode that measures the unique tunneling currents associated with the nucleotide, thereby identifying and resolving the four unique nucleotide types.

However, there are several significant challenges associated with the fabrication of such devices at relatively low cost that can spatially resolve individual nucleotides of each strand, wherein nucleotides are on the order of about 1 nm is size in a transverse direction. One challenge is the ability to fabricate a channel width on the order of about 1 nm to about 10 nm with accuracy and repeatability to obtain tunneling current that is exponential verses distance. Such a channel or pore is sometimes referred to as a nanochannel or nanopore. For example, the signal tunneling current would reduce by a factor of about 1000× if spacing is increased between electrode and base molecule by only about 0.5 nm. A second challenge relates to fabrication of a sensor or nanoelectrode that is on the order of about 1 nm in spacing between the electrodes in order to resolve and detect individual nucleotides (e.g., A,T,C,G) in the DNA strand.

A relatively fast and low-cost genome (DNA), transcriptome (RNA) and proteome (all proteins) sequencing method could lead to the development of personalized medicine (e.g., the ability to target drugs and medical treatments specially to an individual). However, to fabricate a nanochannel for single molecular DNA sequencing is still technically challenging due to the extremely small dimensions involved with the devices used to conduct the sequencing. The devices and methods disclosed herein address at least some of these challenges.

To improve DNA sequencing throughput and lower the cost, direct-reading sequencing device like nanochannel devices based on, for example, (1) semiconductor nanochannel, and (2) transverse electron current measurement may be highly desirable.

A nanochannel structure with a pair of transverse electrodes can be fabricated using conventional nanofabrication processes. A limitation of this structure is the relatively wide nanogap between two electrodes defined by lithography, which is typically in the range of 10 nm to about 30 nm. Ideally a small nanogap between two electrodes on the order of about 0.3 nm and about 2 nm (more particularly on the order of about 1 nm) is preferred to enhance the signal-to-noise ratio during transverse current detection due to the ultrasmall diameter of DNA single strand (~1 nm). The present disclosure relates to a new design for a tunneling electrode for a DNA sequencing device, the tunneling electrode having two transverse electrode member having a uniform, ultrasmall nanogap on the order of about 1 nm (e.g., in the range of about 0.3 nm to about 2 nm). A fabrication process flow to create at least one of the electrode members having a wedge-shape or tapered shape is described as well.

The present disclosure generally relates to DNA sequencing, and more particularly relates to DNA sequencing devices having nanochannels and nanoelectrodes, and related methods of fabricating such devices. The present disclosure may also relate to DNA sequencing using such devices.

The present disclosure also relates to methods for fabricating a DNA nanochannel with a very small tunneling electrode gap (e.g., in the range of about 0.3 nm to about 2 nm), as well as the resultant DNA nanochannel itself and the electrode members of the tunneling electrode (also referred to as a nanoelectrode). The disclosed methods may include fabricating an electrode member having a wedge shaped profile and/or tapered shape in the area of the electrode gap. The tapered or wedge shape of the electrode member may result in less noise in the measured signal, thus resulting in an improved signal-to-noise ratio. The resultant tunneling electrode may be used to measure an electronic signal associated with individual nucleotides of a DNA strand passing through the nanochannel.

The present disclosure also relates to methods for fabricating a wedge shaped or tapered shaped electrode member of a DNA sequencing device. The shape of the electrode member may enhance tunneling current, which may improve detecting individual nucleotides in the DNA strand. One embodiment includes a wedge shaped first electrode (also referred to as a bottom electrode) and a flat or planar second electrode (also referred to as a top electrode) that are used to sequence DNA strands traversing through a gap between the electrodes, as shown in FIG. 1. Methods for fabricating such wedge shaped electrodes include (1) patterning the electrode by liftoff and deposition techniques (see FIGS. 2A-2E), and (2) sharpening and trimming an electrode member by, for example, reactive-ion etching (RIE) or ion-beam etching (IBE) at different incident angles (see FIGS. 3A-3F).

FIGS. 1-3 illustrate example DNA sequencing devices, or portions thereof, and fabrication steps for formation of DNA sequencing devices, or at least portions thereof. While particular fabrication steps, materials, structures and features are shown with references to FIGS. 1-3, other options are available for fabricating the DNA sequencing device. One aspect unique to many of the embodiments disclosed herein is formation of wedge, tapered or pointed feature or cross-sectional shape for one or both of the electrode members of the tunneling electrode of the DNA sequencing device. This feature for the electrode member may help reduce noise in a measured electronic signal associated with a DNA strand passing through the gap between the electrode members. A gap or spacing between the electrode members may be on the order of about 1 nm, and particularly in the range of about 0.3 nm to about 2 nm. The plated tips may also provide a reduced cross-sectional area for the surfaces of the electrode members facing each other as part of the defined gap. This reduced surface area may help reduce the noise in the electronic signal collected by the DNA sequencing device as a DNA strand passes through the electrode gap, thereby improving the signal-to-noise ratio and improving the accuracy of electronic signal measurement, which may lead to improvements in a DNA sequencing method.

FIG. 1 illustrates an example DNA sequencing device 10, or at least a portion of a DNA sequencing device having features in accordance with the present disclosure. The DNA sequencing device 10 may be referred to as a tunneling DNA sequencing device. At least one of a pair of electrodes 14, 16 may have a tapered shape, a tapered or wedge shaped cross-sectional profile, and/or a tapered or wedged-shaped hedge or corner. For example, the bottom electrode 16 may have a cross-sectional shape or profile that is triangular or pointed.

The bottom electrode 16 may be oriented perpendicular to a direction of flow of a DNA strand passing through a gap G between a top electrode 14 and the bottom electrode 16. The direction of flow for the DNA strand may also be the direction of flow through a nanochannel within which the top and bottom electrodes are exposed. The top and bottom electrodes 14, 16 may be arranged in parallel planes with each other, and may be arranged "in plane" with the nanochannel 20. The nanochannel typically has a height H in the range of about 5 nm to about 20 nm, and more particularly in the range of about 10 nm. The gap G between the top and bottom electrodes 14, 16 is typically on the order of about 1 nm, and more particularly in the range of about 0.3 nm to about 2 nm.

Electrodes 14, 16 may comprise a conductive material such as a metal material. In one example, one or more of the electrodes 14, 16 comprises a metal material such as Chromium (Cr).

The top and bottom electrodes 14, 16 are typically electrically connected to a controller or preamp 22. The controller or preamp 22 may detect an electronic signal associated with a DNA strand 4 that is passing through the gap G. The DNA strand has a backbone and a plurality of nucleotides (A,T,C,G). Each of the nucleotides may have a specific resistance or other property that results in a change in electronic signal detected by the electrodes 14, 16 and the controller/preamp 22 as the individual nucleotide pass through the gap G. The DNA strand may be drawn through the gap G by a power source 24 using, for example, an electrophoresis process.

The controller or preamp 22 may use the detected change in electronic current associated with the individual nucleotides to determine an order or sequence of the nucleotides. Thus, the DNA sequencing device 10 may operate to detect and/or determine a DNA sequence, or the sequence of nucleotides of a given DNA strand. By providing a pointed shape for one of the electrodes 14, 16 (e.g., the pointed or wedge shaped of the second electrodes 16 shown in the figures), the DNA sequencing device 10 may experience a lower amount of noise than the electronic signal detected, thereby improving the signal-to-noise ratio and a more certain determination of the DNA sequence.

The second electrode 16 may have a point or edge 18 along a side thereof facing the first electrode 14. The point or edge 18 may be defined at a nanoscale by, for example, a single or small number of atoms, such as a molecule that includes a plurality of atoms. In other examples, the point or edge 18 may have a size on the order of several molecules. The point 18 having one or a plurality of molecules may be formed using one of a plurality of different fabrication methods, including, for example, vapor deposition or the removal of material using, for example, lift-off or dissolving of the material of the electrode 16.

The electrode channel 20 may have a width W typically in the range of about 10 nm to about 20 nm. The height of the electrode channel is typically in the range of about 10 nm to about 20 nm. The electrode channel 20 patterning may be conducted using various lithography tools such as, for example, deep ultraviolet (DUV) lithography, 193 nm lithography, E-beam lithography, nano-imprint lithography (NIL), or the like. Such fabrication methods may be used to form any of the features described herein for the DNA sequencing device 10. The etching of the substrate, resist, or conductive layers may be carried out using, for example, reactive ion etching (RIE).

FIGS. 2A-2E illustrate an example fabrication process for forming the electrode 16 using, for example, an additive process (e.g., thin film deposition and liftoff). Initially, a substrate 12 is coated with a resist material to form a resist layer 26, as shown in FIG. 2A. The resist layer 26 is patterned to form a trench or channel 28, as shown in FIG. 2B. The patterning may be performed using, for example, electron beam lithography.

A conductive material such as metal is then deposited on the resist layer as a conductor deposition 30, as shown in FIG. 2C. Deposition of the conductive material 30 may involve, for example, directional deposition (e.g., using a thermal evaporation process). An example conductive material that is used for depositing as the layer 30 is Chromium (Cr). The conductive material 30 may be deposited within the trench 28 formed in the resist layer 26 to form an electrode member that is positioned on the substrate 12. The electrode 16 may have a tapered construction that is formed due to the closing in of the trench 28 during deposition of the material 30 on the resist layer 26.

The conductive layer 30 formed on the resist layer 26 is then lifted off or otherwise removed, as shown in FIG. 2D. The resist layer 26 may be lifted off or removed in the same or a separate step, as further shown in FIG. 2D. The lift off may include, for example, dissolving the resist layer 26 and/or conductive material 30 using a solvent. FIG. 2D illustrates the electrode 16 positioned by itself on the substrate 12. The electrode 16 is shown in FIG. 2E having a wedge shaped profile and/or wedged cross-sectional shape. The electrode 16 has a pointed tip or edge 18 extending along its length. The electrode 16 may be described as having a triangular cross-sectional shape. The electrode 16 typically extends across an entire width of the channel 20 (see FIG. 1). Accordingly, the electrode 16 is positioned to detect the electronic signal of a DNA strand for passing through the gap G at any location across the width of the channel 20.

Figure 3A:
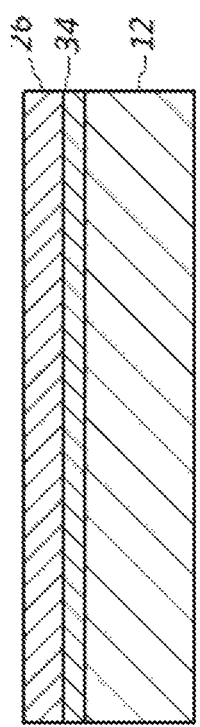
FIGS. 3A-3F show steps of an subtractive process of forming an electrode member for a DNA sequencing device in accordance with the present disclosure.
Figure 3B:
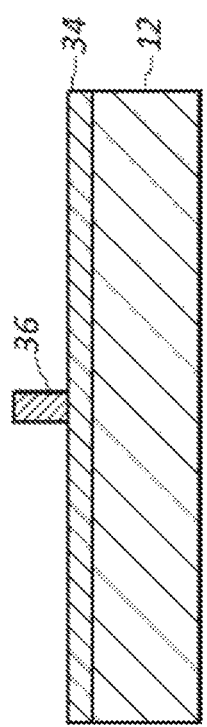
Figure 3C:
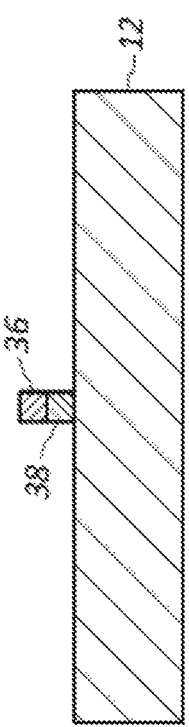
Figure 3D:
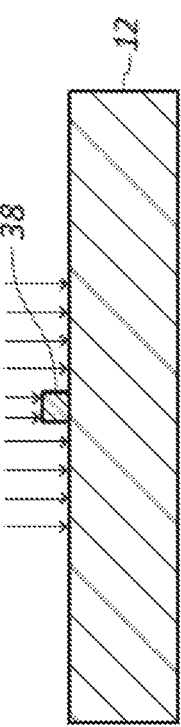

FIGS. 3A-3F illustrate another example fabrication process for forming the bottom electrode 16 using a subtractive process. The subtractive process may include providing, for example, using coating, depositing or the like, a conductive material to form a conductor layer 34 on a substrate 12, as shown in FIG. 3A. The conductive layer 34 may comprise, for example, Chromium or other metal or conductive material. A resist layer 26 is coated on top of the conductive layer 34, as also shown in FIG. 3A. The resist layer 26 is patterned (e.g., using an electron beam lithography process with a negative resist material) to form a strip of resist 36, as shown in FIG. 3B. The pattern (e.g., strip) 36 is transferred onto the conductive layer 34 using, for example, a reactive ion etching (RIE) or ion beam etching (IBE), as shown in FIG. 3C. The resist layer 26 is stripped from the patterned conductive layer 34 using, for example, a resist mask $SiO_2$ RIE method to form an electrode member 38 that is positioned on the substrate, as shown in FIG. 3D.

Figure 3E:
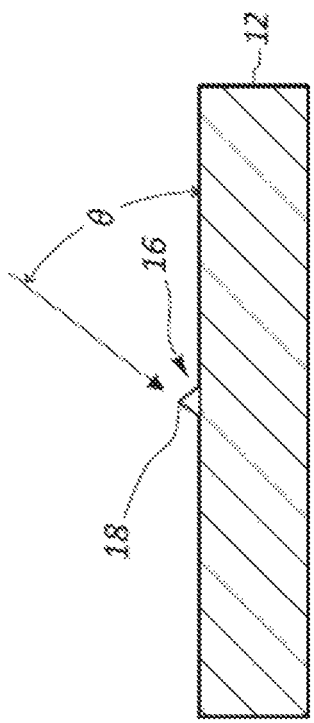
Figure 3F:
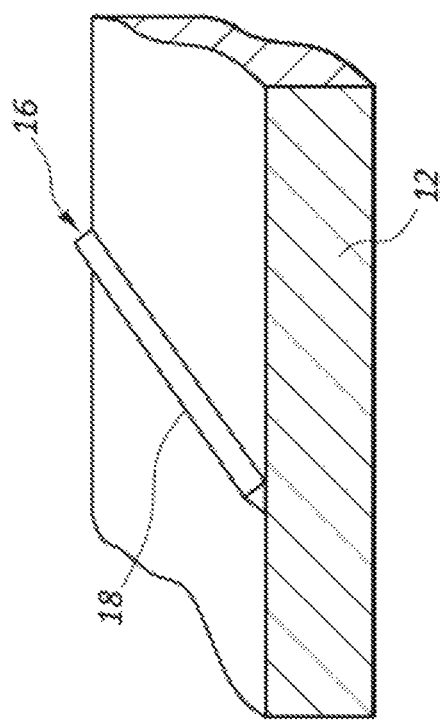

The electrode member 38 may be trimmed to a desired shape such as the wedge or tapered shape disclosed herein for the second electrode 16, as shown in FIG. 3E. The trimming may be performed using, for example, a further RIE or IBE process. The top portion of the electrode 16 may take on a tapered shape due to faster etching at the upper edges 18 of the electrode 16. Controlled shaping of the electrode 16 profile may be achieved through, for example, IBE at different incident angles $\theta$.

The shape of the electrode 16 may be modified or customized using, for example, IBE at different incident angles to create a shape and/or size for the electrode 16 unique for a given DNA sequencing device 10. While the cross-sectional shape of the electrode 16 is shown as a triangle in FIG. 3F, other cross-sectional shapes may be formed in which one or more of the surfaces is contoured, there are more than two exposed surfaces, or the like.

Generally, the substrate 12 may comprise a non-conductive material. In one example, a non-conductive insulator layer may comprise silicone oxide ($SiO_2$). The resist layer (also referred to as a photoresist layer) may comprise, for example, an hydrogen silsesquioxane (HSQ) material, or other high resolution negative tone resist material. The trench 28 may be formed using, for example, etching as described above.

Figure 4:
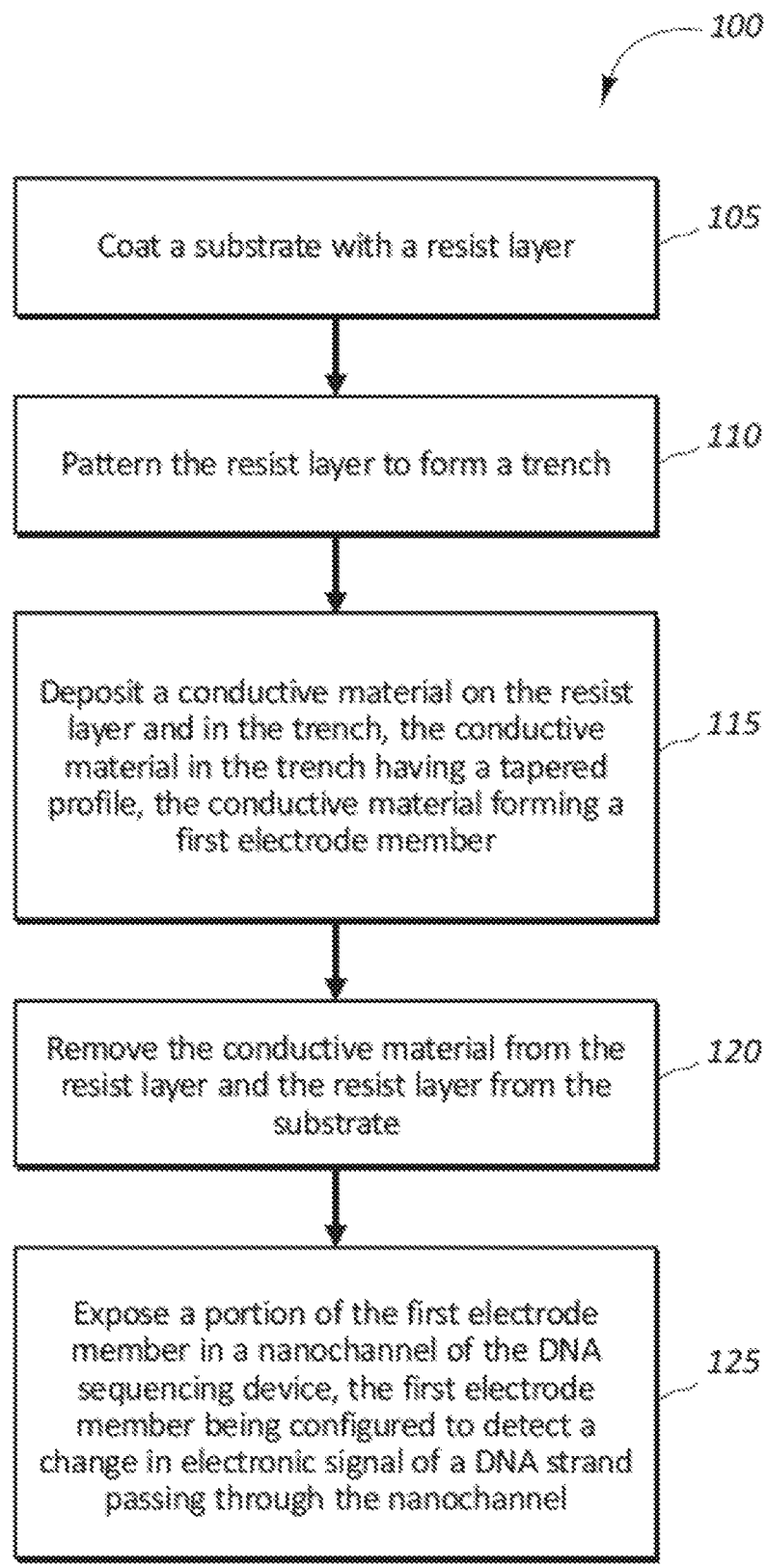
FIG. 4 is a flow chart illustrating an example of a method in accordance with various aspects of this disclosure.

FIG. 4 is a flow chart illustrating an example of a method 100 for fabrication of a DNA sequencing device, in accordance with various aspects of the present disclosure. One or more aspects of the method 100 may be implemented in conjunction with the devices 10 of FIGS. 1-3. In some examples, a computing device may execute one or more sets of code to control functional elements of the DNA sequencing devices disclosed herein to perform one or more of the functions described below. Additionally, or alternatively, computing devices and/or storage devices may perform one or more of the functions described below using special-purpose hardware.

At block 105, method 100 may include coating a substrate with a resist layer. Block 110 may include patterning the resist layer to form a trench or channel. Block 115 includes depositing a conductive material on the resist layer in the trench, the conductive material in the trench having a tapered or pointed profile. The conductive material may form a first electrode member. At block 120, the method 100 may include removing the conductive material from the resist layer and the resist layer from the substrate. Block 125 includes exposing a portion of the first electrode member in a nanochannel of the DNA sequencing device, the first electrode member being configured to detect a change in electrode signal of the DNA strand passing through the nanochannel.

The method 100 may further include patterning the resist layer using electron beam lithography. The position of the conductive material may include directional deposition of the conductive material. Deposition of the conductive material may include thermal evaporation of the conductive material. Lifting off the conductive material may include dissolving the conductive material in a solvent. The method 100 may include trimming the first electrode member to sharpen the tapered profile of the first electrode member, such as to a pointed shape or tip. Trimming the first electrode member may include using reactive ion etching (RIE) or ion beam etching (IBE) to remove portions of the first electrode member. The method 100 may include forming a second electrode member, and exposing a portion of the second electrode member in the nanochannel at a location spaced apart from the first electrode member to form an electrode gap through which the DNA strand passes.

Figure 5:
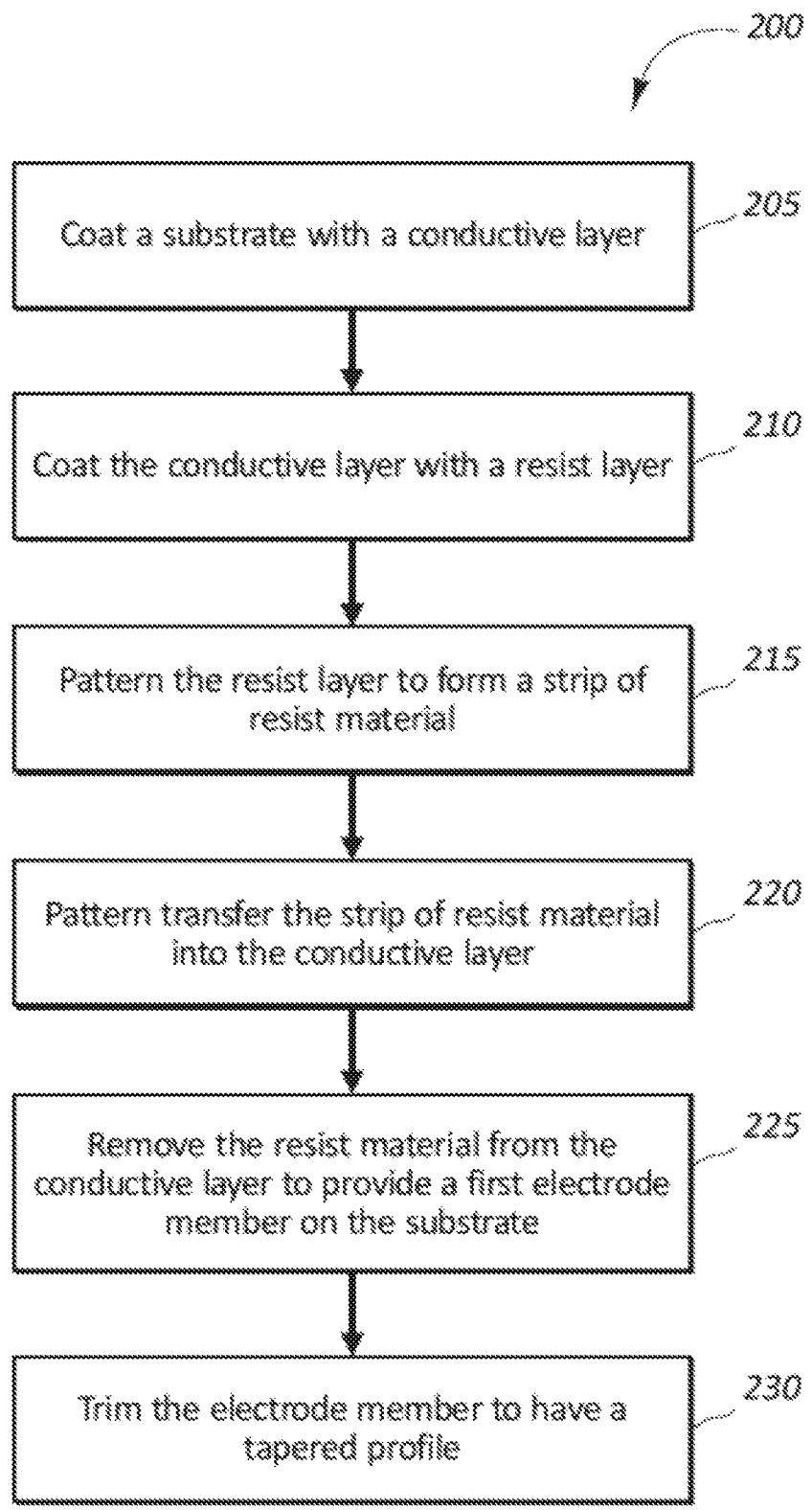
FIG. 5 is a flow chart illustrating an example of a method in accordance with various aspects of this disclosure.

FIG. 5 is a flow chart illustrating an example of a method 200 for fabrication of a DNA sequencing device, in accordance with the various aspects of the present disclosure. One or more aspects of the method 200 may be implemented in conjunction with the devices 10 described with reference to FIGS. 1-3. In some examples, a computing device may execute one or more sets of code to control functional elements of the DNA sequencing device as disclosed herein to perform one or more of the functions described below. Additionally, or alternatively, computing devices and/or storage devices may perform one or more of the functions described below using special purpose hardware.

The method 200 may include, at block 205, coating a substrate with a conductive layer. Block 210 includes coating the conductive layer with a resist layer. Block 215 includes patterning the resist layer to form a strip of resist material. Block 220 includes pattern transferring the strip of resist material into the conductive layer. Block 225 includes removing the resist material from the conductive layer to provide a first electrode member on a substrate. Block 230 includes trimming the electrode member to a tapered profile.

The method 200 may further include pattern transferring using reactive ion etching (RIE) or ion beam etching (IBE) to remove portions of the conductive layer. Removing the resist material may include using $O_2$ reactive ion etching (RIE) to remove remaining portions of the resist material from the conductive layer. Trimming the electrode member may include using reactive ion etching (RIE) or ion beam etching (IBE) to remove portions of the electrode member. Trimming the electrode member may include using ion beam etching (IBE) at multiple incident angles.

Figure 6:
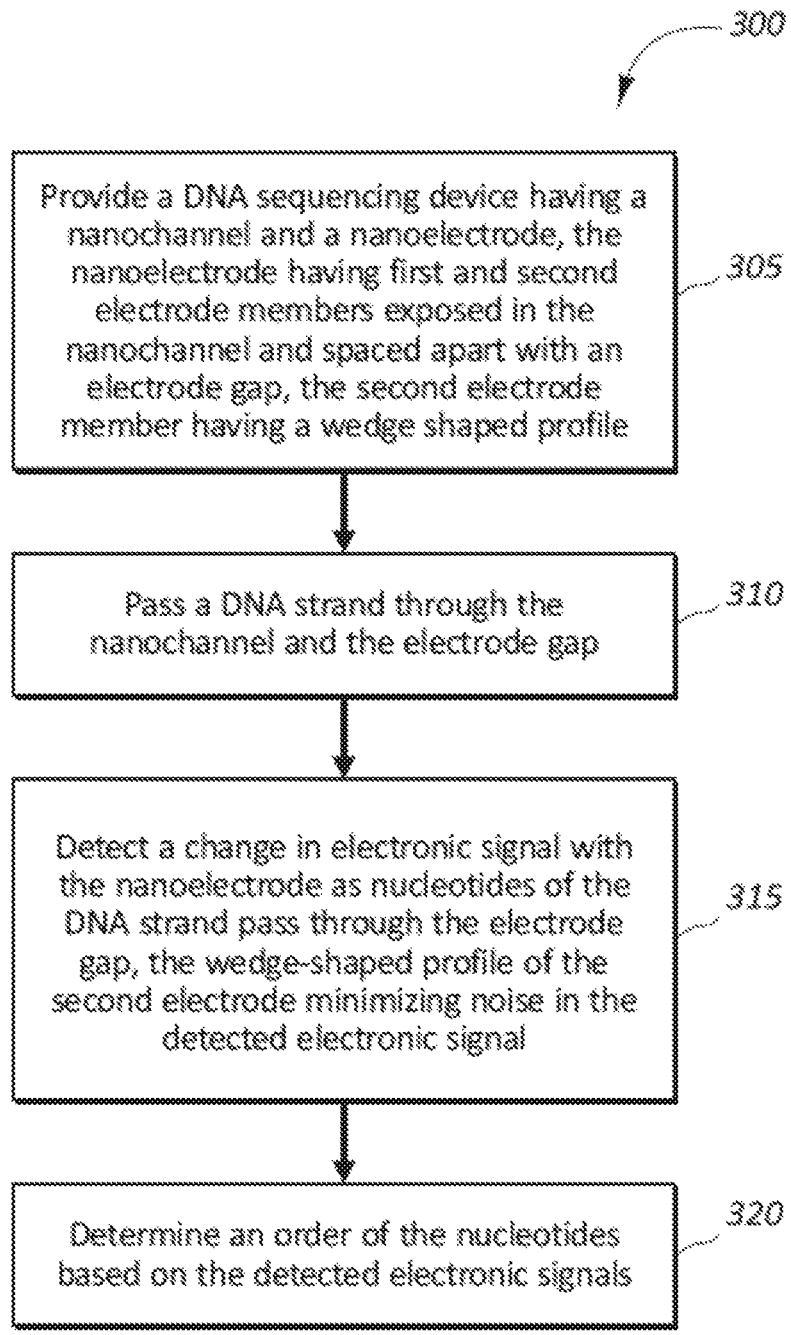
FIG. 6 is a flow chart illustrating an example of a method in accordance with various aspects of this disclosure.

FIG. 6 is a flow chart illustrating an example of a method 300 for DNA sequencing, in accordance with various aspects of the present disclosure. One or more aspects of the method 300 may be implemented in conjunction with the devices 10 described with reference to FIGS. 1-3. In some examples, a computing device may execute one or more sets of code to control functional elements of the DNA sequencing devices disclosed herein to perform one or more of the functions described below. Additionally, or alternatively, computing devices and/or storage devices may perform one or more of the functions described below using special purpose hardware.

The method 300 may include, at block 305, providing a DNA sequencing device having a nanochannel and a nanoelectrode, the nanoelectrode having first and second electrode members exposed in the nanochannel and spaced apart with an electrode gap, the second electrode member having a wedge shaped, tapered and/or pointed profile. Block 310 includes passing a DNA strand through the nanochannel and the electrode gap. Block 315 includes detecting a change in the electronic signal with the nanoelectrode as nucleotides of the DNA strand pass through the electrode gap, the wedge shaped profile of the second electrode resulting in minimized noise in the detected electronic signal. Block 320 includes determining an order of the nucleotides based on the detected signals.

The example methods 100, 200, 300 may, in other embodiments, include fewer or additional steps that those illustrated in FIGS. 4-6. Further, many other methods and method steps may be possible based on the disclosures provided herein.

Figure 7:
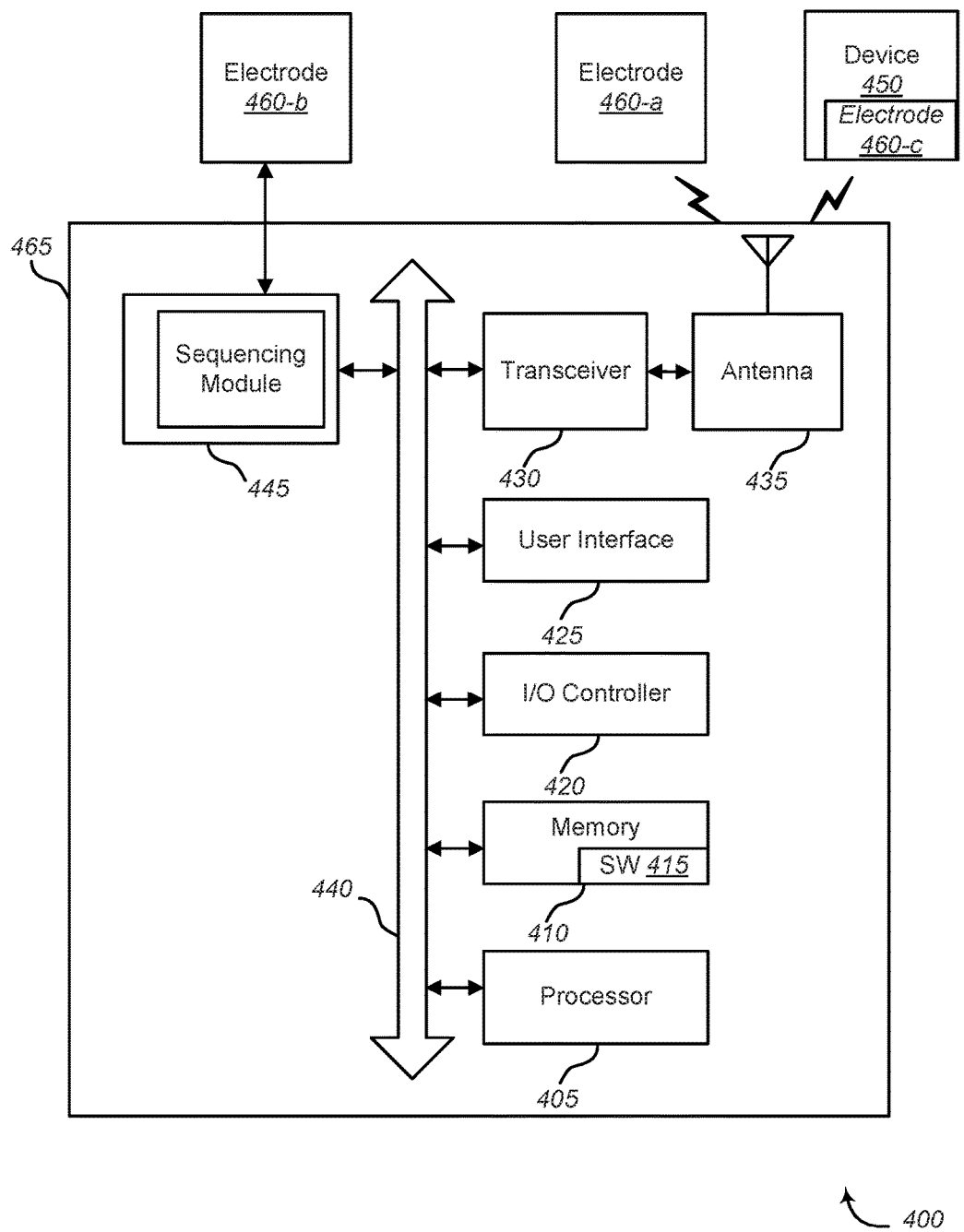
FIG. 7 shows a diagram of a system in accordance with various aspects of this disclosure.

FIG. 7 shows a system 400 for use with the DNA sequencing devices and systems shown in FIGS. 1-3. System 400 may include a control panel 465. Control panel 465 may be equivalent at least in part to a controller, control unit, processor or the like for use with the devices described above with reference to FIGS. 1-3. Control panel 465 may include sequencing module 445. The sequencing module 445 may provide communications with one or more electrodes 460-a, 460-b, 460-c (also referred to as sensors or devices) directly or via other communication components, such as a transceiver 430 and/or antenna 435. The electrodes 460 may represent one or more of the electrodes 14, 16, or pairs of such electrodes in any of the embodiments described above. The sequencing module 445 may perform or control various operations associated with, for example, the electrodes 14, 16, actuators, controllers, or other components of the DNA sequencing devices and related systems as described above with reference to FIGS. 1-7.

Control panel 465 may also include a processor module 405, and memory 410 (including software/firmware code (SW) 415), an input/output controller module 420, a user interface module 425, a transceiver module 430, and one or more antennas 435 each of which may communicate, directly or indirectly, with one another (e.g., via one or more buses 440). The transceiver module 430 may communicate bi-directionally, via the one or more antennas 435, wired links, and/or wireless links, with one or more networks or remote devices. For example, the transceiver module 430 may communicate bi-directionally with one or more of device 450 and/or electrodes 460-a, 460-c. The device 450 may be components of the DNA sequencing devices and related systems and devices described with reference to FIGS. 1-3, or other devices in communication with such systems and devices. The transceiver 430 may include a modem to modulate the packets and provide the modulated packets to the one or more antennas 435 for transmission, and to demodulate packets received from the one or more antennas 435. In some embodiments (not shown) the transceiver may be communicate bi-directionally with one or more of device 450, remote control device 455, and/or electrodes 460-a, 460-c through a hardwired connection without necessarily using antenna 435. While a control panel or a control device (e.g., 465) may include a single antenna 435, the control panel or the control device may also have multiple antennas 435 capable of concurrently transmitting or receiving multiple wired and/or wireless transmissions.

In some embodiments, one element of control panel 465 (e.g., one or more antennas 435, transceiver module 430, etc.) may provide a connection using wireless techniques, including digital cellular telephone connection, Cellular Digital Packet Data (CDPD) connection, digital satellite data connection, and/or another connection.

The signals associated with system 400 may include wireless communication signals such as radio frequency, electromagnetics, local area network (LAN), wide area network (WAN), virtual private network (VPN), wireless network (using 302.11, for example), 345 MHz, Z-WAVE®, cellular network (using 3G and/or LTE, for example), and/or other signals. The one or more antennas 435 and/or transceiver module 430 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 435 may receive signals or information specific and/or exclusive to itself. In other embodiments, each antenna 435 may receive signals or information not specific or exclusive to itself.

In some embodiments, one or more electrodes 460 (e.g., voltage, inductance, resistance, current, force, temperature, etc.) or devices 450 may connect to some element of system 400 via a network using one or more wired and/or wireless connections. In some embodiments, the user interface module 425 may include an audio device, such as an external speaker system, an external display device such as a display screen, and/or an input device (e.g., remote control device interfaced with the user interface module 425 directly and/or through I/O controller module 420).

One or more buses 440 may allow data communication between one or more elements of control panel 465 (e.g., processor module 405, memory 410, I/O controller module 420, user interface module 425, etc.).

The memory 410 may include random access memory (RAM), read only memory (ROM), flash RAM, and/or other types. The memory 410 may store computer-readable, computer-executable software/firmware code 415 including instructions that, when executed, cause the processor module 405 to perform various functions described in this disclosure (e.g., initiating an adjustment of a lighting system, etc.). Alternatively, the software/firmware code 415 may not be directly executable by the processor module 405 but may cause a computer (e.g., when compiled and executed) to perform functions described herein. Alternatively, the computer-readable, computer-executable software/firmware code 415 may not be directly executable by the processor module 405 but may be configured to cause a computer (e.g., when compiled and executed) to perform functions described herein. The processor module 405 may include an intelligent hardware device, e.g., a central processing unit (CPU), a microcontroller, an application-specific integrated circuit (ASIC), etc.

In some embodiments, the memory 410 can contain, among other things, the Basic Input-Output system (BIOS) which may control basic hardware and/or software operation such as the interaction with peripheral components or devices. For example, the sequencing module 445, and other modules and operational components of the control panel 465 used to implement the present systems and methods may be stored within the system memory 410. Applications resident with system 400 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 430, one or more antennas 435, etc.).

Many other devices and/or subsystems may be connected to one or may be included as one or more elements of system 400. In some embodiments, all of the elements shown in FIG. 7 need not be present to practice the present systems and methods. The devices and subsystems can be interconnected in different ways from that shown in FIG. 7. In some embodiments, an aspect of some operation of a system, such as that shown in FIG. 7, may be readily known in the art and are not discussed in detail in this application. Code to implement the present disclosure can be stored in a non-transitory computer-readable medium such as one or more of system memory 410 or other memory. The operating system provided on I/O controller module 420 may be iOS®, ANDROID®, MS-DOS®, MS-WINDOWS®, OS/2®, UNIX®, LINUX®, or another known operating system.

The transceiver module 430 may include a modem configured to modulate the packets and provide the modulated packets to the antennas 435 for transmission and/or to demodulate packets received from the antennas 435. While the control panel or control device (e.g., 465) may include a single antenna 435, the control panel or control device (e.g., 465) may have multiple antennas 435 capable of concurrently transmitting and/or receiving multiple wireless transmissions.

In some embodiments, the DNA sequencing device and systems described herein may be used to collect electronic signals associated with the nucleotides of a DNA strand passing through the gap between electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

U.S. Prov. App. No. 62/453,270, titled "SINGLE-MOLECULE DNA SEQUENCING METHOD USING CONFINED NANO-FLUIDIC CHANNEL AND SUB-NANOMETER ELECTRODE GAP," filed on 1 Feb. 2017, and U.S. patent application Ser. No. 15/886,442, titled "SINGLE-MOLECULE DNA SEQUENCING METHOD USING CONFINED NANO-FLUIDIC CHANNEL AND SUB-NANOMETER ELECTRODE GAP," filed on 1 Feb. 2018.

U.S. Prov. App. No. 62/453,398, titled "NANOFLUIDIC CHANNEL OPENING SIZE CONTROL USING ACTUATION," filed on 1 Feb. 2017, and U.S. patent application Ser. No. 15/886,483, titled "NANOFLUIDIC CHANNEL OPENING SIZE CONTROL USING ACTUATION," filed on 1 Feb. 2018.

U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.

U.S. Prov. App. No. 62/453,307, titled "METHOD TO FABRICATE A NANOCHANNEL FOR DNA SEQUENCING BASED ON NARROW TRENCH PATTERNING PROCESS," filed on 1 Feb. 2017, and U.S. patent application Ser. No. 15/886,533, titled "METHOD TO FABRICATE A NANOCHANNEL FOR DNA SEQUENCING BASED ON NARROW TRENCH PATTERNING PROCESS," filed on 1 Feb. 2018.

U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560, titled "FABRICATION OF A DEVICE FOR SINGLE-MOLECULE DNA SEQUENCING USING SIDEWALL LITHOGRAPHY," filed on 1 Feb. 2018.

U.S. Prov. App. No. 62/453,339, titled "FABRICATION OF A NANOCHANNEL FOR DNA SEQUENCING USING ELECTRICAL PLATING TO ACHIEVE TUNNELING ELECTRODE GAP," filed on 1 Feb. 2017, and U.S. patent application Ser. No. 15/886,581, titled "FABRICATION OF A NANOCHANNEL FOR DNA SEQUENCING USING ELECTRICAL PLATING TO ACHIEVE TUNNELING ELECTRODE GAP," filed on 1 Feb. 2018.

U.S. Prov. App. No. 62/453,346, titled "NANOSTRUCTURES TO CONTROL DNA STRAND ORIENTATION AND POSITION LOCATION FOR TRANSVERSE DNA SEQUENCING," filed on 1 Feb. 2017, and U.S. patent application Ser. No. 15/886,608, titled "NANOSTRUCTURES TO CONTROL DNA STRAND ORIENTATION AND POSITION LOCATION FOR TRANSVERSE DNA SEQUENCING," filed on 1 Feb. 2018.

U.S. Prov. App. No. 62/453,329, titled "DIRECT SEQUENCING DEVICE WITH A TOP-BOTTOM ELECTRODE PAIR," filed on 1 Feb. 2017, and U.S. patent application Ser. No. 15/886,685, titled "DIRECT SEQUENCING DEVICE WITH A TOP-BOTTOM ELECTRODE PAIR," filed on 1 Feb. 2018.

U.S. Prov. App. No. 62/453,376, titled "MICRO AND NANOFLUIDIC CHANNEL CONTROLLED ACTUATION TO OPEN CHANNEL GAP," filed on 1 Feb. 2017.

U.S. Prov. App. No. 62/469,393, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2017, and U.S. patent application Ser. No. 15/886,736, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2018.

U.S. Prov. App. No. 62/469,409, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2017, and U.S. patent application Ser. No. 15/886,723, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A method of forming a DNA sequencing device, the method comprising:
    coating a substrate with a resist layer;
    patterning the resist layer on the substrate to form a trench in the resist layer, the trench having an open end at a surface of the resist layer and extending to the substrate;
    depositing a conductive material on the resist layer and in the trench, the conductive material forming a first electrode member in the trench, the first electrode having a tapered profile more narrow at the open end of the trench than at the substrate;
    removing the conductive material from the resist layer and the resist layer from the substrate;
    exposing a portion of the first electrode member in a nanochannel of the DNA sequencing device, the first electrode member being configured to detect a change in electronic signal of a DNA strand passing through the nanochannel.

2. The method of claim 1, wherein patterning the resist layer includes using electron beam lithography for the patterning.

3. The method of claim 1, wherein deposition of the conductive material includes directional deposition of the conductive material.

4. The method of claim 1, wherein deposition of the conductive material includes thermal evaporation of the conductive material.

5. The method of claim 1, wherein lifting off the conductive material includes dissolving the conductive material in a solvent.

6. The method of claim 1, further comprising trimming the first electrode member to sharpen the tapered profile of the first electrode member.

7. The method of claim 6, wherein trimming the first electrode member includes using reactive ion etching (RIE) or ion beam etching (IBE) to remove portions of the first electrode member.

8. The method of claim 1, further comprising:
forming a second electrode member;
exposing a portion of the second electrode member in the nanochannel at a location spaced apart from the first electrode member to form an electrode gap through which the DNA strand passes.

9. A method of forming a DNA sequencing device, the method comprising:
coating a substrate with a conductive layer;
coating the conductive layer with a resist layer;
patterning the resist layer to form a strip of resist material;
pattern transferring the strip of resist material into the conductive layer to form a conductive strip;
removing the resist material from the conductive strip to provide a first electrode member on the substrate;
after removing the resist material, trimming the first electrode member to have a tapered profile.

10. The method of claim 9, wherein pattern transferring includes using reactive ion etching (RIE) or ion beam etching (IBE) to remove portions of the conductive layer.

11. The method of claim 9, wherein removing the resist material includes using $O_2$ reactive ion etching (RIE) to remove remaining portions of the resist material from the conductive layer.

12. The method of claim 9, wherein trimming the first electrode member includes using ion beam etching (IBE) at multiple incident angles.

13. A method of claim 9, wherein the tapered profile includes a wedge-shaped profile.

\* \* \* \* \*